(12) United States Patent
Ziechner

(10) Patent No.: US 10,094,848 B2
(45) Date of Patent: Oct. 9, 2018

(54) PIPETTING APPARATUS AND METHODS FOR AN AUTOMATIC ANALYSIS DEVICE

(71) Applicant: Siemens Healthcare Diagnostics Products GmbH, Marburg (DE)

(72) Inventor: Eike Ziechner, Wehrheim (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 14/733,736

(22) Filed: Jun. 8, 2015

(65) Prior Publication Data
US 2015/0355212 A1 Dec. 10, 2015

(30) Foreign Application Priority Data

Jun. 10, 2014 (EP) .................................. 14171721

(51) Int. Cl.
| | |
|---|---|
| *G01N 35/10* | (2006.01) |
| *B01L 3/02* | (2006.01) |
| *B01L 9/00* | (2006.01) |
| *G01N 35/00* | (2006.01) |

(52) U.S. Cl.
CPC .............. *G01N 35/10* (2013.01); *B01L 3/021* (2013.01); *B01L 9/543* (2013.01); *G01N 35/00693* (2013.01); *G01N 35/1004* (2013.01); *G01N 35/1011* (2013.01); *G01N 35/1079* (2013.01); *B01L 3/0275* (2013.01); *B01L 2200/04* (2013.01); *B01L 2200/148* (2013.01); *B01L 2300/0672* (2013.01); *B01L 2300/0838* (2013.01); *Y10T 436/11* (2015.01)

(58) Field of Classification Search
None
See application file for complete search history.

(56) References Cited

U.S. PATENT DOCUMENTS

| | | | |
|---|---|---|---|
| 5,314,825 A | 5/1994 | Weyrauch et al. | |
| 6,360,794 B1 | 3/2002 | Turner | |
| 7,585,678 B2 | 9/2009 | Sigrist | |
| 2007/0015276 A1 | 1/2007 | LeBlanc et al. | |
| 2011/0020919 A1* | 1/2011 | Fulton ................... | B01L 3/0275 435/287.2 |

FOREIGN PATENT DOCUMENTS

| | | |
|---|---|---|
| CN | 1936589 A | 3/2007 |
| EP | 1767950 | 3/2007 |
| EP | 2420848 A2 | 2/2012 |

OTHER PUBLICATIONS

European Search Report of European Application No. 14171721.5 dated Nov. 24, 2014.
Chinese Search Report of Chinese Application No. 201510295495X dated Aug. 23, 2017.

* cited by examiner

*Primary Examiner* — Samuel P Siefke
(74) *Attorney, Agent, or Firm* — Dugan & Dugan, PC

(57) ABSTRACT

The invention relates to a pipetting apparatus for an automatic analysis device, which is particularly stable and allows simple and error-proof replacement of the pipetting apparatus and, therefore, particularly reliable operation of the analysis device. To this end, an essentially frustoconical fastening body is arranged around an axial region of the needle body.

13 Claims, 4 Drawing Sheets

PIPETTING APPARATUS AND METHODS FOR AN AUTOMATIC ANALYSIS DEVICE

CROSS REFERENCE TO RELATED APPLICATION

This claims priority to European Patent Application No. EP 14171721.5, filed Jun. 10, 2014, which is hereby incorporated by reference herein in its entirety for all purposes.

FIELD

The invention relates to a pipetting system for an automatic analysis device, comprising a pipetting apparatus and a holder therefor. It furthermore relates to a method for adjusting an adjustment point assigned to the pipetting apparatus in an automatic analysis device.

BACKGROUND

Numerous detection and analysis methods for determining physiological parameters in body fluid samples or other biological samples are carried out in an automated fashion in large numbers in corresponding automatic analysis devices. Modern analysis devices are capable of carrying out a multiplicity of detection reactions and analyses with a sample. In order to be able to carry out a multiplicity of examinations in an automated fashion, it is necessary to transfer small quantities of liquid to a multiplicity of positions by automated pipetting. For example, aliquots of the sample liquids must be taken from the sample vessels or accurately predetermined subquantities of reagents must be taken from the reagent containers and transferred into the reaction vessel intended for the examination in question. To this end, depending on the intended purpose, a plurality of corresponding pipetting systems is provided in the analysis device.

Such a pipetting system conventionally comprises a pipetting needle on an actively mobile element, for example a transport arm, the pipetting needle being fastened to a needle holder on the transport arm. The pipetting needle is configured as a hollow needle, which can take and deliver defined quantities of sample in an automated fashion. The pipetting needle is conventionally introduced along the mid-axis of a vessel, where appropriate piercing of a resilient stopper may occur in the case of closed vessels, and the pipetting needle is immersed into the liquid. The immersion is registered by means of a corresponding sensor, and the intended quantity of liquid is aspirated with controlled pressure. The quantity taken is then supplied to the corresponding analysis. The pipetting needle is subsequently washed in a corresponding device and is ready for its next use.

If an error in terms of positioning occurs during operation of the pipetting system, unintended contact, i.e., a crash, may take place. Even slight contact can cause errors in the immersion registration. Because of the sometimes high forces acting, however, damage to the needle or the object touched may also occur, or unintended transfer of sample material and therefore vitiation of the test results may take place. It is therefore absolutely necessary to avoid such crashes. Precisely because of the small diameters of the openings of the vessels used, namely a few millimeters, this can be ensured only by exact adjustment of the vessel positions and of the pipetting needle.

One problem is that the pipetting needle constitutes a disposable part, which regularly needs to be replaced. In particular, the frequent piercing of vessel stoppers leads to metal abrasion and bending of the needle. When the needle is replaced, however, the new needle tip has a different position in space, and the risk arises that the needle tip will depart so far from the setpoint position that the small openings of the vessels will be missed. Even a deviation of a few millimeters is sufficient for this.

To date, therefore, replacement of a pipetting needle has typically entailed comprehensive readjustment. With gauges, the new pipetting needle is fitted by hand and the adjustment is checked by comprehensive tests. Adjustable needles, which are fastened by means of wedge bearings, have been developed for this. A wedge bearing is respectively fitted to the needle on the right and on the left, the wedge of the needle having a smaller wedge angle than the counterbearing wedge of the needle holder. There is therefore only line contact on the right and on the left. This on the one hand cannot be measured accurately heightwise, and on the other hand it still allows a tilting movement of the needle. This tilting movement is spatially adjusted by means of setscrews. After adjustment, the setscrews are sealed with screw lacquer. Sometimes, pipetting middles are also adjusted by eye, struts of the frame or other straight housing parts being used for orientation. The vertical should in this case always be determined in two directions per needle. Such a method, however, is on the one hand error-prone and on the other hand expensive, since it typically cannot be carried out by the user himself; instead the replacement of the pipetting needle must be performed by a specially trained service engineer. Furthermore, the bearing is not especially stable and cannot withstand large forces, so that the needle slipping out during operation is not ruled out, and this makes even more frequent adjustment necessary.

SUMMARY

It is therefore an object of the invention to provide a pipetting apparatus and a holder therefor, which are particularly stable and allow simple, error-proof and adjustment-free replacement of the pipetting needle, and which therefore allow particularly reliable operation of an analysis device.

In respect of the pipetting needle, this object is achieved in that a fastening body, which is used for fastening the pipetting needle on a needle holder, is arranged around an axial region of the needle body, the fastening body essentially being configured as a conical frustum, the vertex of which lies in the longitudinal axis of the needle body.

In respect of the needle holder, the object is achieved by the latter comprising a cavity configured essentially as a conical frustum, the imaginary vertex of which lies in the mid-axis of the access opening of the holder for the needle body.

This has the advantage that the same position of the needle is reproduced after replacement of a pipetting needle, because only one single exact position of the needle is possible.

This is possible on the basis of a conical holder. To this end, the needle holder comprises a cavity which is configured conically, i.e., in the shape of a cone or a conical frustum. The access opening for the needle in this case lies at the vertex of the conical frustum. A fastening body, which is exactly shaped to match the cavity and is therefore likewise conical, is provided on the needle. During mounting, the needle is inserted into the opening and the fastening body as an inner cone is inserted exactly into the cavity and is thus fixed.

BRIEF DESCRIPTION OF THE DRAWINGS

The invention will be explained in more detail with the aid of drawings, in which.

Figure 1:
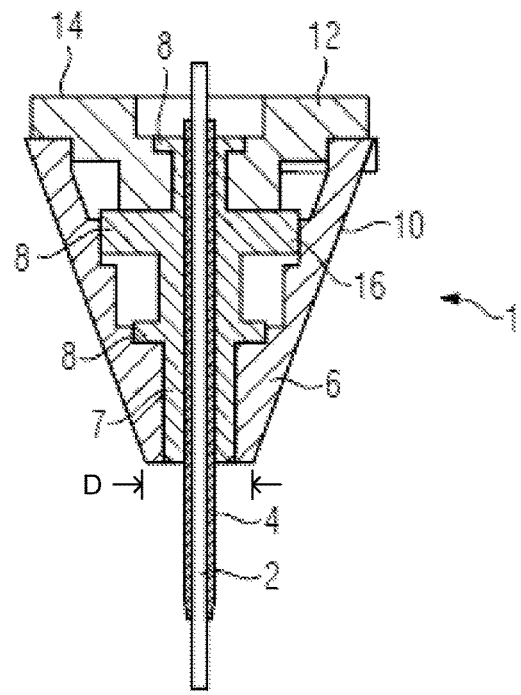
FIG. 1 shows a sectional representation of a pipetting apparatus for an automatic analysis device.

Parts which are the same are provided with the same references in all the figures.

DETAILED DESCRIPTION

The present invention relates to a pipetting apparatus for an automatic analysis device. The pipetting apparatus comprises an essentially hollow-cylindrical needle body and a fastening body arranged around an axial region of the needle body in order to fasten the needle body on a holder of the automatic analysis device. The fastening body is essentially configured as a conical frustum, the imaginary vertex of which lies in the longitudinal axis of the hollow-cylindrical needle body.

Advantageously, the fastening body is configured as a right conical frustum.

The present invention also relates to a holder for such a pipetting apparatus. To this end, the holder comprises an opening for the needle body and has a cavity essentially configured as a conical frustum, the imaginary vertex of which lies in the mid-axis of the opening.

Correspondingly, the cavity in the holder is advantageously also configured as a right conical frustum.

In principle, any conical shape ensures an accurately matching position of the needle and the needle holder. For example, the cone may have a circle, an ellipse, a regular or irregular polygon, for example a triangle, a quadrilateral, a pentagon, a hexagon, a heptagon, an octagon or a nonagon as its base surface. In other embodiments, the cone may have a star, for example with pointed and/or rounded vertices, as its base surface, or the base surface may be bounded by any closed planar curve. The cone may be a right cone or an oblique cone. The cone may also be a conical frustum.

In a preferred embodiment, the cone is a right circular cone. A right circular cone is a body of rotation, which has the advantage that it can be produced easily and with particularly high accuracy on a lathe. Depending on the materials and the precise production method, accuracies in the thousandth of a millimeter range are possible in CNC (Computerized Numerical Control) machines. With a right circular cone as the fitting shape, therefore, a particularly high accuracy of the position can be achieved. The tolerances are therefore reduced, so that the requirements described in the introduction for the spatial positioning are satisfied. The vertex angle of the cone should in this case be selected in such a way that the self-locking is not too great, so that the inner cone, i.e., the fastening body with the needle, can easily be removed and replaced. At the same time, however, the angle should also be configured in such a way that the self-locking is great enough for the repositioning to be ensured exactly, and for there to be no play in the needle holder.

The cone of the holder, the inner cone of the fastening body of the pipetting apparatus, the gauge and the needle may, for example, be made of plastic, metal, glass, stone, wood, or other suitable materials or material combinations. The cone of the holder and the inner cone of the fastening body of the pipetting apparatus may in this case be made of the same material or different materials.

Preferably, both the cone of the holder and the inner cone of the fastening body of the pipetting apparatus are made of plastic. In such a configuration, for example, greater self-locking between these parts may not be desirable, for example, so that the inner cone of the fastening body can be removed more easily from the cone of the holder, which may for example be advantageous when changing a gauge or a pipetting needle.

Preferably, the gauge or the needle is, for example, made of metal and the inner cone of the fastening body of the pipetting apparatus is made of plastic. With such a configuration, for example, greater self-locking between the needle and the inner cone of the fastening body of the pipetting apparatus may be desirable, in order to establish a stronger and less readily separable connection between the gauge or the needle and the inner cone of the fastening body of the pipetting apparatus.

With respect to the fastening body, the diameter D (see FIG. 1) and/or the height of the conical frustum is advantageously more than three times, preferably more than five times the diameter of the needle body. In this way, sufficient holding of the fastening body in the holder is ensured.

In another advantageous configuration, the fastening body comprises a holding element which extends perpendicularly to the longitudinal axis of the hollow-cylindrical needle body and is preferably configured as a rectangular or cylindrical holding pin. Since a right circular cone is a body of rotation, although there is fixing in the axial and radial directions, there is not fixing in the azimuthal direction. For this reason, for example, a cutting edge of the tip of the hollow needle is not fixed. This is ensured by a holding element extending perpendicularly to the longitudinal axis of the needle body.

In this way, for example, the orientation of a needle opening and/or a venting groove of a needle can be established, which may be advantageous, for example, when washing the needle in a washing station, for example, because of a special orientation of nozzles in the washing station. Furthermore, the correct orientation of the needle opening may be advantageous, for example, when wiping off drops on a vessel edge.

When the pipetting apparatus is installed in the holder, the holding element engages in a recess which is introduced into the lateral surface of the conical cavity and is configured in order to receive the holding element of the fastening body. In this way, exact fixing is achieved in the circumferential direction as well. Advantageously, the recess has a rectangular cross section or it is configured as a wedge-shaped notch, the vertex of the wedge being directed toward the vertex of the cone or conical frustum. In this way, on the one hand, installation is facilitated since the new needle does not immediately have to be oriented exactly, but even in the case of approximately accurate orientation it slips into the correct position because of the converging edges of the wedge shape, and on the other hand exact positioning is also ensured.

In another advantageous configuration, the holder for the pipetting apparatus comprises a fixing element which is formed in order to exert a force in the direction of the opening for the needle and is arranged in the region of the base surface of the conical cavity. Screws, clips and various other arrangements, which ultimately have the common feature that they press the frustoconically shaped fastening body with the needle in the axial direction into the cavity and therefore fix it there, are suitable as fixing elements.

The present invention also relates to a pipetting system which comprises a pipetting apparatus according to the invention and/or a holder according to the invention for the pipetting apparatus.

The present invention furthermore relates to an automatic analysis device which comprises a pipetting system according to the invention.

Advantageously, an analysis device according to the invention comprises a contact body for adjusting an assigned adjustment point, the contact body having two edges which are mirror-symmetrical with respect to a mirror axis extending through the adjustment point.

Advantageously, the edges of the contact body are not mutually parallel.

In another embodiment of the analysis device, the contact body is configured as a washing station for the needle body of the pipetting apparatus.

The invention furthermore relates to the use of a pipetting apparatus according to the invention for adjusting an adjustment point assigned to the pipetting apparatus or for positioning a contact body by means of an adjustment point assigned to the contact body in an automatic analysis device.

The described exact fixing of the needle in the needle holder makes it possible to carry out the required basic adjustment of the needle holder as well as the adjustment of stations which the needle approaches, for example, holders of blood sampling tubes, needle washing station, etc., in an (at least partially) automated fashion with the needle itself. Owing to the exact positioning of the needle, its tip can be used as an adjustment mark. This may be done both during first setup of the automatic analysis device and during subsequent replacement of said approach stations. To this end, it is necessary to be able to accurately determine the exact coordinates of the respective adjustment points and to be able to store them in a controller of the analysis device.

When a pipetting apparatus is used for adjusting an adjustment point assigned to the pipetting needle in a described analysis device, in order to determine a first coordinate of the adjustment point, a contact body having two edges which are mirror-symmetrical with respect to a mirror axis extending through the adjustment point is therefore advantageously arranged, the needle body is moved perpendicularly to the mirror axis onto the two edges, the respective contact points are determined, and the first coordinate is determined as the midpoint between the two contact points. Such a contact body with two edges may, for example, be an opening arranged on a needle washing station in the manner of a template. By movement onto the opposite inner edges, the first coordinate can be determined by movement in one dimension as the midpoint of the distance between the edges.

In another advantageous configuration of the use of a pipetting apparatus, the edges of the contact body are not mutually parallel, and the second coordinate is determined from the geometry of the edges and the distance between the two contact points. This is because if the two edges are not mutually parallel, together with said requirement for mirror symmetry, an isosceles triangle is formed (depending on the length of the sides and the exact shape of the contact body, optionally truncated to a trapezoid shape). In this shape, the mirror axis intersects the first coordinate point of the contact point. The first coordinate can thus be determined. In addition, however, any position on the mirror axis is also assigned a distance between the edges and therefore a distance perpendicularly to the mirror axis. If the geometry of the contact body is known to the controller, with only one movement from one edge to the opposite edge, both coordinates can be determined, namely the first coordinate as the center between the end positions and the second coordinate from the length of the distance between the end positions and the geometry of the contact body.

During the adjustment process, a measurement cylinder may be used instead of the pipetting needle. A separate measurement cylinder for the adjustment, which has a fastening apparatus identical to that of the needle and the tip of which lies at the same position as that of the needle, has the advantage that it can be formed in an optimized way for the adjustment and thereby makes the adjustment process more accurate. For example, a measurement cylinder may be formed with a larger diameter and solidly, so that it exhibits scarcely any elastic behavior when touching a contact point, as could be the case with a hollow needle. Furthermore, the measurement cylinder can be processed particularly accurately in terms of tolerances, so that the accuracy of the position determination is improved even further.

The advantages achieved with the invention consist, in particular, in that by the use of a fastening body based on a conical shape, exact reproducibility of the position of a hollow needle in an analysis device when replacing the pipetting apparatus is ensured, so that readjustment after replacement is no longer necessary. A single factory adjustment is sufficient, all other inaccuracies then resulting only from the tolerances of the needle itself and with respect to the needle holder. These are to be ensured by an accurate manufacturing and quality process. It is therefore even possible to use the needle itself as a plug gauge in order to adjust other modules themselves, for example, a washing station for the pipetting needles.

Advantageously, the contact body for adjusting an assigned adjustment point is configured as a washing station for a pipetting needle or is connected to a washing station for a pipetting needle or is integrated into a washing station for a pipetting needle.

The adjustment of the pipetting needle may thus advantageously be carried out immediately before, during and/or after a washing process. This is particularly advantageous since no additional and therefore time-consuming distances need to be covered for the position determination of the pipetting needle, so that the sample throughput of an analysis device can be increased considerably.

FIG. 1 shows a sectional representation of a pipetting apparatus 1. The pipetting apparatus 1 comprises a hollow-cylindrical metal needle body 2, which has a constant outer diameter starting from the needle tip (not shown) and has a thickening 4 in the region shown in FIG. 1. At the opposite end from the needle tip, the needle body 2 is exposed so that a tube can be connected thereto, which allows the pipetting apparatus 1 to be operated in an automatic analysis device by pressure or reduced pressure with and without control fluids, so that—controlled by a controller—defined quantities of sample can be taken and delivered in an automated fashion.

To this end, the pipetting apparatus 1 is inserted along the mid-axis of the respective vessel, where appropriate piercing of a resilient stopper occurs in the case of closed vessels, and the needle body 2 is immersed into the liquid. The immersion is registered by means of an immersion sensor, and the predetermined quantity is aspirated with controlled pressure. The quantity taken is then supplied to the corresponding analysis. The needle body 2 is subsequently washed in a washing station and is ready for its next use.

The pipetting apparatus 1 comprises a three-part fastening body 6 around the longitudinal axis 5 of the needle body 2 in the region of the thickening 4. The fastening body 6 in this case consists of an inner part 7 firmly connected to the needle body 2, an outer part 10 and a base surface part 12. The inner part 7 comprises a hollow-cylindrical body enclosing the needle body 2 and, extending concentrically therefrom, disks 8 of different radii and with partially chamfered edges with different chamfer angles. These will not be described in detail since they are essentially used only to ensure a form-fit connection of the needle body 2 to the outer part 10 and to the base surface part 12 of the fastening body 6.

The outer part 10 of the fastening body 6 has the outer shape of a right circular conical frustum. It is produced by turning on a lathe. The mid-axis of the outer part 10 corresponds to the longitudinal axis 5 of the needle body 2, and the imaginary vertex 15 of the cone points toward the tip of the needle body 2. The base surface of the circular conical frustum is formed by the base surface part 12 of the fastening body 6, which comprises a circular disk 14 forming the base surface and rotationally symmetrical structures 16, which are in turn used for form-fit connection to the inner part 7.

Figure 2:
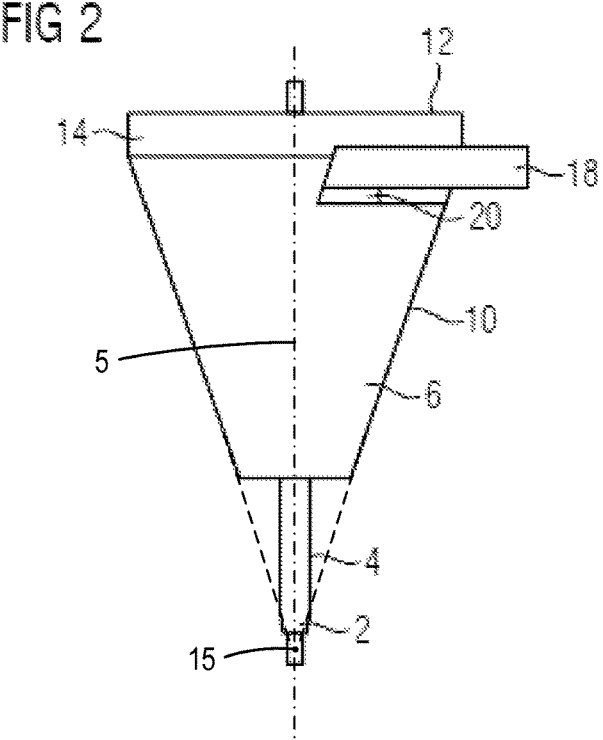
FIG. 2 shows a side view of the pipetting apparatus.

In addition, the base surface part 12 of the fastening body 6 also comprises a holding element 18 which is represented clearly in FIG. 2, the plan view of the pipetting apparatus 1 of FIG. 1. The holding element 18 has a cuboid shape and extends with breaking of the rotational symmetry outward perpendicularly to the longitudinal axis 5 of the needle body 2 through an interruption 20 of the outer part 10. What is essential for the holding of the pipetting apparatus 1 in a holder is the conical outer shape of the fastening body 6 and of the holding element 18.

Figure 3:
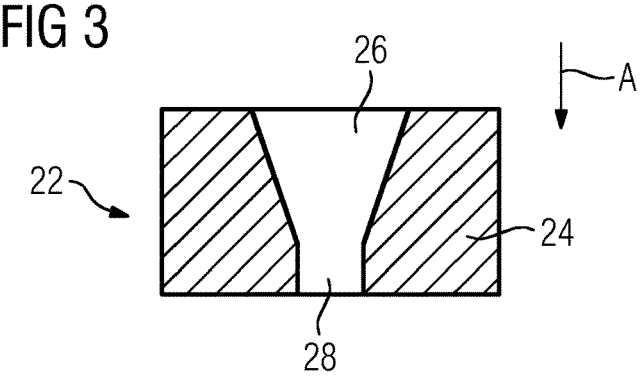
FIG. 3 shows a sectional representation of a holder for a pipetting apparatus.
Figure 4:
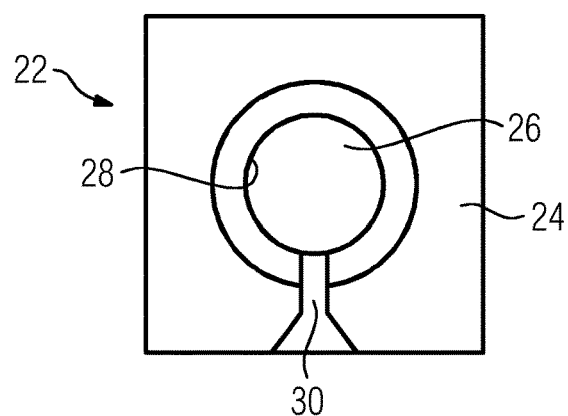
FIG. 4 shows a plan view of the holder.
Figure 5:
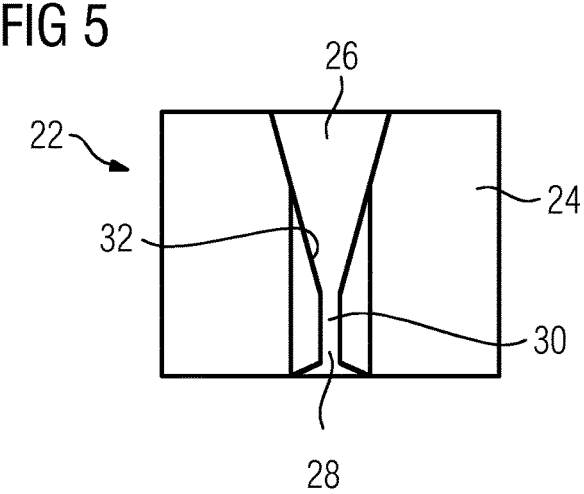
FIG. 5 shows a side view of the holder.

The holder 22, in which the pipetting apparatus 1 is fixed on a mobile arm of the automatic analysis device, is represented in FIGS. 3 to 5. FIG. 3 shows a lateral sectional representation of the holder 22. The holder 22 essentially comprises a cuboid block 24 with a square base surface. A cavity 26, which is adapted to the outer shape of the fastening body 6 and has an identical conical shape, albeit in negative, is formed in the block. In other words, a circular opening which forms the base surface of the conical frustum is introduced into the upper side of the block 24. Starting from the opening, the cavity 26 tapers into the block 24 and thus forms a conical frustum. This is followed concentrically by a cylindrical opening 28 as far as the opposite side of the block 24.

The holder 22 is shown in FIG. 4 in plan view from the direction A shown in FIG. 3. Here, it is shown that the block 24 comprises a straight gap 30 extending over the entire height, which makes it possible to introduce the pipetting apparatus 1 laterally.

Lastly, FIG. 5 shows a side view of the holder 22. Because of the conical shape of the cavity 26 in the middle of the block 24, the gap 30 at the upper end forms a recess 32, which tapers in the shape of a wedge together with the cavity 26.

The fixing of the pipetting apparatus 1 in the holder 22 is carried out by the needle body 2 of the pipetting apparatus 1 being introduced laterally through the gap 30 into the holder 22, so that its longitudinal axis 5 lies approximately in the mid-axis of the cavity 26. The pipetting needle is subsequently guided downward, so that the fastening body 6 is guided into the cavity 26 and the holding element 18 is guided into the recess 32. By the accurate fit of the cavity 26, the fastening body 6, or the recess 32, and the holding element 18, fixing of the pipetting apparatus 1 is achieved, which also allows reproducibly accurate positioning during replacement.

By a detachable fixing element (not shown in detail), which exerts a force in the direction of the needle tip on the fastening body 6 and is arranged in the region of the circular disk 14, for example, screws or a holding clip, the pipetting apparatus 1 is definitively fixed in the holder 22.

The reproducible accurate fixing of the pipetting apparatus 1 makes it possible for only a single adjustment of the pipetting apparatus 1, or of the holder 22, to be necessary at the factory. During subsequent replacement of the pipetting apparatus 1, exact positioning of the replacement needle is ensured by the described shape.

Figure 6:
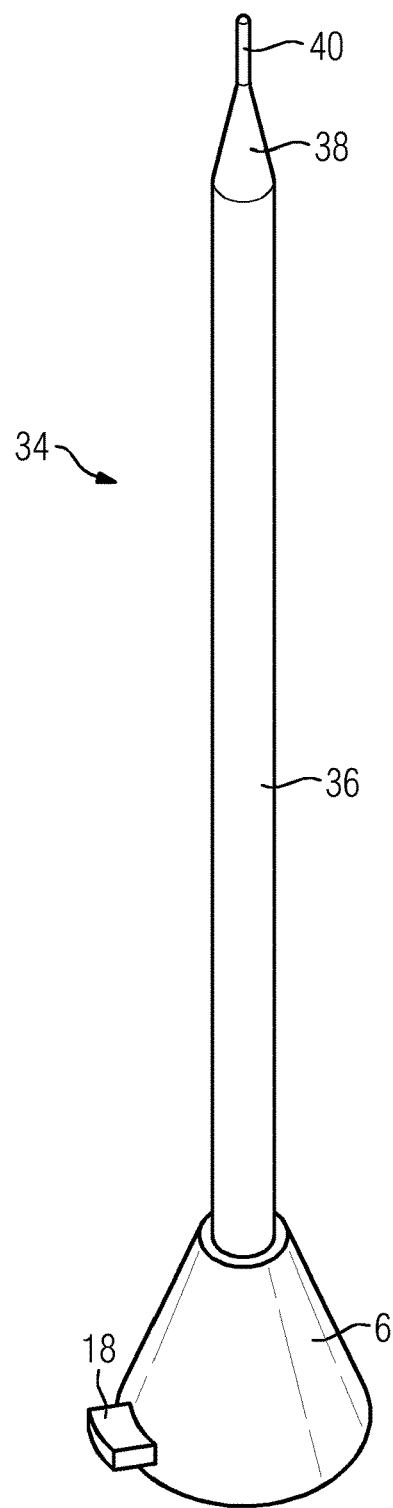
FIG. 6 shows a view of a measurement cylinder.

Advantageously, the adjustment of the holder 22 is carried out by means of a measurement cylinder 34, which is fitted into the holder 22 instead of the pipetting apparatus 1 during the adjustment and which is shown in a view in FIG. 6, in a similar way to the adjustment of the pipetting apparatus 1.

The measurement cylinder 34 correspondingly comprises a fastening body 6 and a holding element 18. Instead of the needle body 2, however, it has a thicker solid cylinder body 36, which has a conical termination 38 with a thin measurement tip 40. The measurement cylinder 34 is torsionally stiff and is manufactured particularly accurately with high precision. It is therefore suitable for particularly accurate adjustment.

Figure 7:
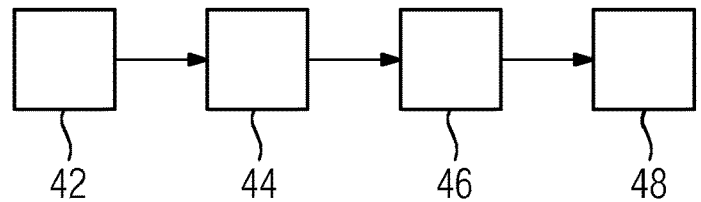
FIG. 7 shows a flowchart of a first adjustment method.

Adjustment of the pipetting apparatus 1 is carried out by the method schematically represented in FIG. 7. The starting point is a component, for example, a retainer for a lid of a blood sampling tube, which has two symmetrical edges. The arm which can be moved in an automated fashion, and on which the pipetting apparatus 1 is fixed by means of a holder 22, firstly travels in step 42 in a first direction, for example, from the left, with the pipetting apparatus 1 onto the first edge of the retainer, until contact is established. The position is stored. In step 44, the pipetting apparatus 1 travels upward, then onto the other side of the retainer and down again there. In step 46, the pipetting apparatus 1 travels in the opposite direction, i.e., in this case from the right, against the second edge until contact is established. This position is also stored. In step 48, a first coordinate of the midpoint is determined as an adjustment point from the central position between the stored positions.

For a spatial direction perpendicular thereto, the same method may be applied. Furthermore, gaps of light on the left and right of the pipetting apparatus 1 may be used for manual visual adjustment. In each case, the position of the pipetting apparatus 1 is known and can be used for adjustment of other components, for example, the washing station, as described below.

Figure 8:
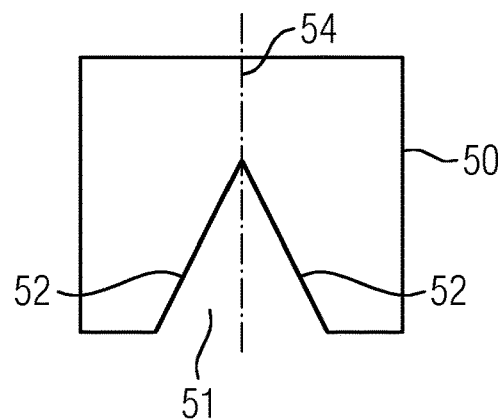
FIG. 8 shows a schematic representation of a measurement triangle.

A contact body 50, which is represented in FIG. 8, is arranged as centrally as possible over the entry opening of the washing station or any other station into which the pipetting needle is immersed. This contact body has a wedge-shaped projection 51 with two edges 52, which form an isosceles triangle. The contact body 50 is symmetrical with respect to a mirror axis 54.

Figure 9:
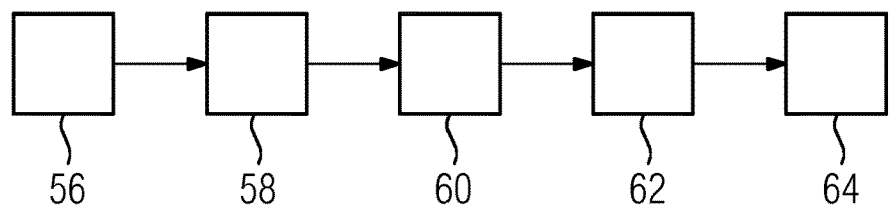
FIG. 9 shows a flowchart of a second adjustment method.

The adjustment method is schematically represented in FIG. 9. The pipetting apparatus 1 travels into the triangular projection 51. In step 56, it is guided perpendicularly to the mirror axis 54 onto the first edge 52, then in step 58 in the opposite direction onto the second edge 52. As previously in the method according to FIG. 7, in step 60 the first coordinate of the midpoint, i.e., the position of the mirror axis 54, can be determined in step 60 from the average value because of the symmetry.

The geometry of the contact body 50 is known to the controller. With the angle of the triangle, the diameter of the pipetting apparatus 1 and the length of the distance between the two edges 52, the controller then also determines the position on the mid-axis, i.e., the coordinate perpendicular to the first coordinate. It is thus possible to determine two coordinates with only one distance. The washing station is then moved in step 64 in a way corresponding to the difference and the method is repeated until the washing station is positioned exactly. The value of the position is stored.

During adjustment of the holder 22 by means of the measurement cylinder 34, after adjustment of all positions, the measurement cylinder 34 is replaced with the pipetting apparatus 1. The method may also be used to carry out a check of the adjustment during operation of the automatic analysis device. The state of wear of the pipetting apparatus 1 can also be identified in this way by large adjustment deviations.

LIST OF REFERENCES

1 pipetting apparatus
2 needle body
4 thickening
5 longitudinal axis
6 fastening body
7 inner part
8 disk
10 outer part
12 base surface part
14 circular disk
15 vertex
16 structures
18 holding element
20 interruption
22 holder
24 block
26 cavity
28 opening
30 gap
32 recess
34 measurement cylinder
36 cylindrical body
38 termination
40 measurement tip
42, 44, 46, 48 step
50 contact body
51 projection
52 edge
54 mirror axis
56, 58, 60, 62, 64 step
A direction
D diameter

The invention claimed is:

1. A pipetting apparatus for an automatic analysis device, comprising a needle and a fastening body, wherein the needle includes a hollow-cylindrical needle body having two ends and a constant outer diameter between the two ends, and the fastening body is arranged around an axial region of the needle body and is configured to fasten the needle body on a holder of the automatic analysis device, wherein the fastening body is configured as a conical frustum, the imaginary vertex of which lies in a longitudinal axis of the hollow-cylindrical needle body, and the two ends of the needle body each extend beyond the fastening body, the fastening body comprising a holding pin extending perpendicularly to the longitudinal axis of the hollow-cylindrical needle body in order to prevent rotation of the hollow-cylindrical needle body about the longitudinal axis; wherein:

the fastening body comprises a base surface part, an inner part, and an outer part having a hollow conical frustum body sized to receive the inner part therein, the inner part comprising a hollow-cylindrical body enclosing the needle and comprising a plurality of disks each extending concentrically therefrom and each having a radius different than others of the plurality of disks to provide a form-fit connection to the outer part and to the base surface part.

2. The pipetting apparatus as claimed in claim 1, wherein the diameter and/or the height of the conical frustum is more than three times the diameter of the needle body.

3. The pipetting apparatus as claimed in claim 1, wherein the diameter and/or the height of the conical frustum is more than five times the diameter of the needle body.

4. A holder configured for the pipetting apparatus of claim 1, the holder having an opening for the hollow-cylindrical needle body, the holder having a cavity extending from the opening configured as a conical frustum, the imaginary vertex of which lies in the mid-axis of the opening, wherein the holder has a recess configured to receive the holding pin, the recess formed in a lateral surface of the cavity.

5. The holder as claimed in claim 4, wherein the recess is configured in the shape of a wedge.

6. The holder as claimed in claim 4, wherein the holder has a fixing element formed in order to exert a force in the direction of the opening.

7. A pipetting system comprising the pipetting apparatus of claim 1 and the holder of claim 4.

8. An automatic analysis device comprising the pipetting apparatus of claim 1, the holder of claim 4, and a controller.

9. The automatic analysis device as claimed in claim 8, further comprising a contact body for adjusting an assigned adjustment point, the contact body having two edges which are mirror-symmetrical with respect to a mirror axis extending through the adjustment point.

10. The automatic analysis device as claimed in claim 9, wherein the two edges of the contact body are not mutually parallel.

11. The automatic analysis device as claimed in claim 9, wherein the contact body is configured as a washing station for the needle body of the pipetting apparatus, and the two edges form an isosceles triangle.

12. The pipetting apparatus as claimed in claim 1, wherein the holding pin is configured as a rectangular or cylindrical holding pin.

13. The pipetting apparatus as claimed in claim 1, wherein the holding pin has a cuboid shape.

* * * * *